United States Patent
Wolf et al.

(10) Patent No.: US 7,604,006 B2
(45) Date of Patent: Oct. 20, 2009

(54) CONTROL UNIT FOR FLOW REGULATION

(75) Inventors: Harald Wolf, Ruemmelsheim-Burg Layen (DE); Andreas Fachinger, Ober-Olm (DE); Holger Memmesheimer, Ockenheim (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 838 days.

(21) Appl. No.: 10/747,341

(22) Filed: Dec. 29, 2003

(65) Prior Publication Data

US 2004/0261792 A1 Dec. 30, 2004

Related U.S. Application Data

(63) Continuation of application No. PCT/EP02/07040, filed on Jun. 26, 2002.

(30) Foreign Application Priority Data

Jul. 2, 2001 (DE) ................................ 101 31 516

(51) Int. Cl.
*A61M 15/00* (2006.01)
*A61M 13/00* (2006.01)

(52) U.S. Cl. ......................... 128/203.12; 128/203.15; 128/204.22

(58) Field of Classification Search ............ 128/203.12, 128/203.14, 203.15, 204.22, 204.21, 204.26, 128/204.23, 204.19, 204.29, 205.12; 600/529, 600/532

See application file for complete search history.

(56) References Cited

U.S. PATENT DOCUMENTS

| | | | | |
|---|---|---|---|---|
| 3,968,430 A | * | 7/1976 | Maas | 600/521 |
| 4,558,710 A | * | 12/1985 | Eichler | 600/533 |
| 4,561,443 A | * | 12/1985 | Hogrefe et al. | 607/31 |
| 4,730,500 A | | 3/1988 | Hughes | |
| 5,320,108 A | * | 6/1994 | Cloutier | 600/529 |
| 5,669,877 A | | 9/1997 | Blomquist | |
| 5,887,586 A | | 3/1999 | Dahlbaeck et al. | |
| 6,220,242 B1 | * | 4/2001 | Wallin | 128/203.12 |
| 6,688,304 B2 | * | 2/2004 | Gonda et al. | 128/200.14 |
| 6,854,460 B1 | * | 2/2005 | Shofner et al. | 128/203.15 |

FOREIGN PATENT DOCUMENTS

| | | |
|---|---|---|
| DE | 197 14 684 A1 | 10/1998 |
| DE | 197 20 701 A1 | 11/1998 |
| FR | 2 800 288 A1 | 5/2001 |
| GB | 2 351 155 A1 | 12/2000 |

OTHER PUBLICATIONS

International Search Report for PCT/EP02/07040 mailed Nov. 15, 2002.
G. Belforte et al; A Tester for Artificial Respirators; Measurement (2000) vol. 27 pp. 241-250; Elsevier Science Ltd.

(Continued)

*Primary Examiner*—Danton DeMille
(74) *Attorney, Agent, or Firm*—Michael P. Morris; David L. Kershner; Mary-Ellen M. Devlin

(57) ABSTRACT

The invention relates to a control unit for flow regulation for use in an apparatus for testing the delivery of a dose of powder from a powder inhaler, a collecting tube for use in conjunction with the control unit and an apparatus containing the control unit and the collecting tube.

6 Claims, 13 Drawing Sheets

OTHER PUBLICATIONS

"Zubereitungen zur Inhalation-Aerodynamische Beurteilung Feiner Teichen" European Pharmacopoeia, 3rd Edition, Supplement pp. 101-112, 1537-1543 (2000).

"Metered-Dose Inhalers and dry powder Inhalers" Aerosols/ Physical Tests, US Pharmacopoeia 24, pp. 1896-1912.

* cited by examiner

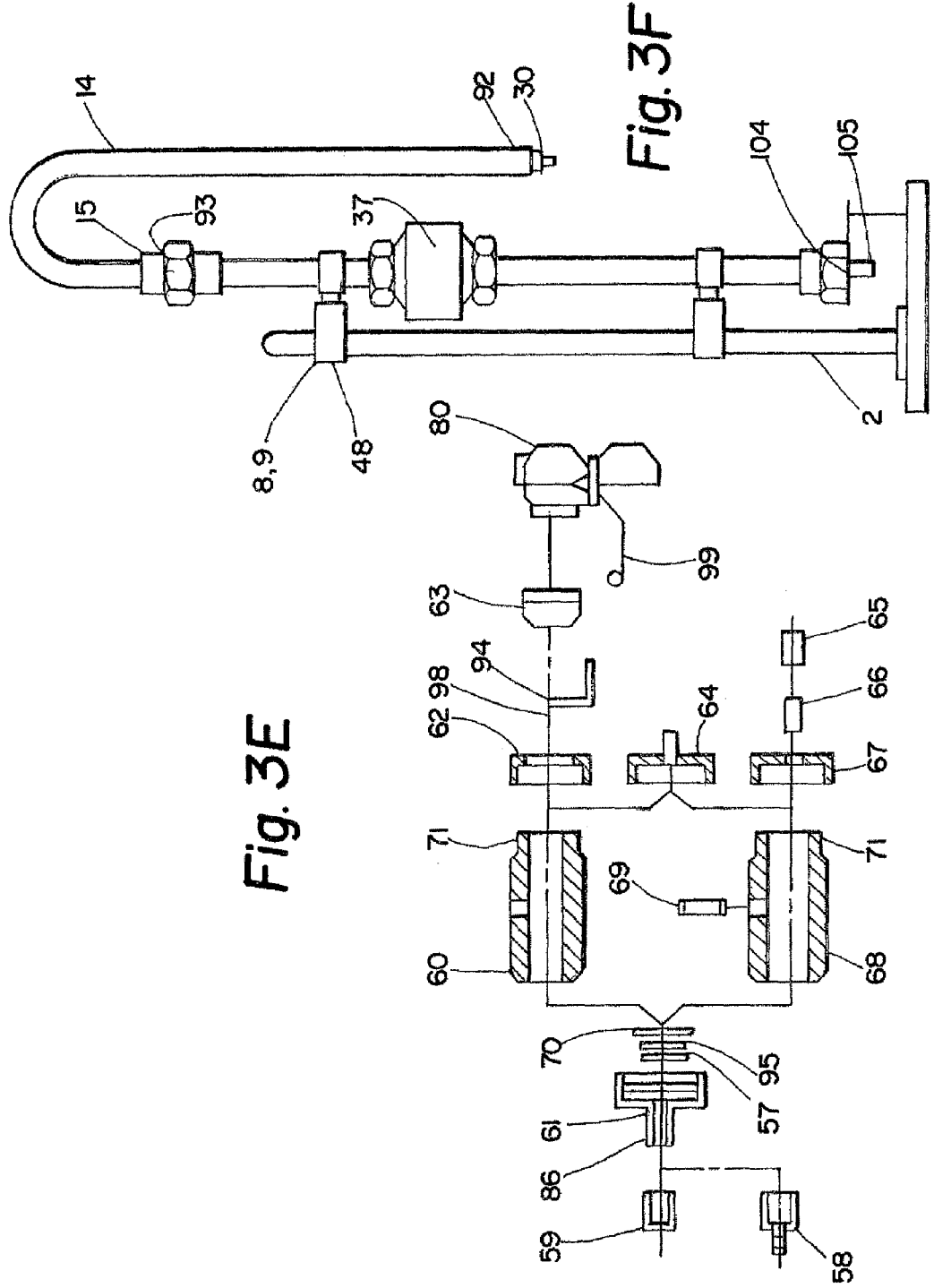

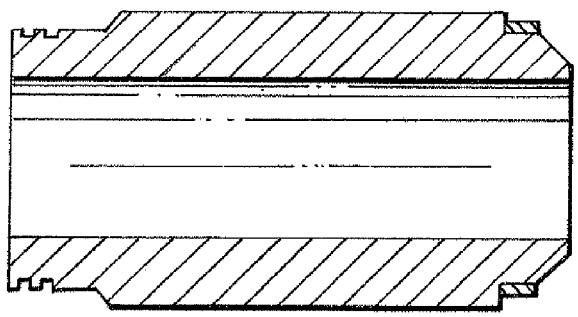
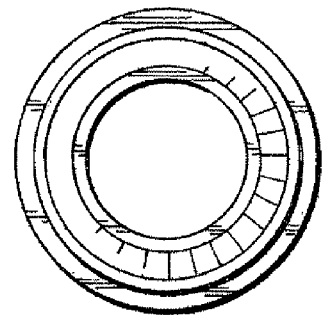
Fig. 6AFig. 6B
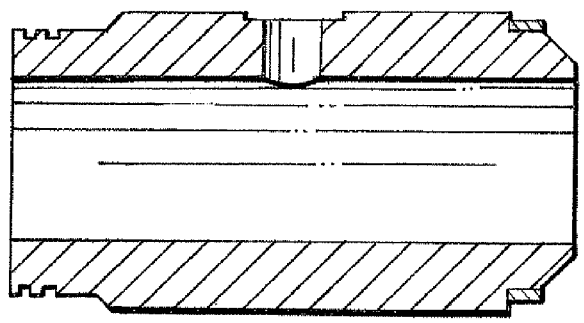
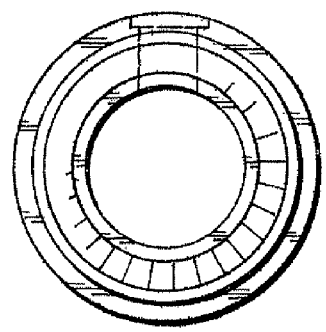
Fig. 6CFig. 6D

CONTROL UNIT FOR FLOW REGULATION

CROSS-REFERENCE TO RELATED APPLICATIONS

This application is a continuation of PCT/EP02/07040 filed Jun. 26, 2002.

BACKGROUND OF THE INVENTION

The present invention relates to a control unit for flow regulation which is used in conjunction with a collecting tube for determining the uniformity of a dose of drug delivered from a powder inhaler or in conjunction with a (cascade) impactor for determining the distribution of the aerodynamic fine fraction in this delivered dose. The invention also relates to measuring and dose collecting tubes for use in conjunction with the control unit, and a process for determining the above-mentioned parameters using the control unit and collecting tubes.

With regard to the effectiveness of a drug which is released as an inhalable powder from an inhaler (e.g. a single dose inhaler such as the "HandiHaler®" or the "Ingelheim Inhaler" or a multi-dose inhaler), the amount of active substance delivered and its aerodynamic particle size distribution are crucial. These test parameters serve to indicate the quality of the pharmaceutical composition and can be determined in the course of stability tests. The methods of measuring these parameters are standardised in US Pharmacopoeia 24, page 1896 ff. (hereinafter referred to as USP) and European Pharmacopoeia, 3rd Edition, Supplement 2000, page 1540 ff and page 101 ff (hereinafter referred to as EP). The pharmacopoeias specify the physical parameters which are to be maintained during measurement (e.g. the level of suction to be applied in order to deliver the dose of drug) and the basic construction of the devices to be used for these measurements. The EP and USP contain for example the diagrammatic drawings shown in FIGS. 1 and 2.

The principle of determining the quantity of active substance delivered or the aerodynamic particle size distribution is based on the active substance being delivered from an inhaler in a defined flow volume. The quantity of powder released is caught in a special device (dose collecting tube or cascade impactor) and then subjected to quantitative analysis.

As can be seen from FIGS. 1 and 2, the apparatus diagrammatically illustrated in EP/USP consists of a suction unit in the form of a vacuum pump, a two-way magnetic valve controllable by a time switch, a throughflow control valve and a collecting tube or an impactor. The vacuum and two-way magnetic valve, two-way magnetic valve and throughflow control valve and the throughflow control valve and collecting tube or cascade impactor are connected to one another. P1, P2 and P3 show positions where pressure gauges can be mounted.

When carrying out the measurements a defined under pressure is produced in the collecting tube or in the cascade impactor by the suction of the vacuum pump. As a result of the underpressure a specific flow volume flows through the inhaler, causing particles of powder to be drawn out of the inhaler into the dose collecting tube or the impactor. The quantity of active substance collected therein is then quantified by a suitable method, for example HPLC.

In order to be able to carry out the measurements under standardised reproducible conditions, a defined flow volume with which the dosage of drug is delivered from the inhaler must be guaranteed, in particular. The EP/USP specify a flow volume of 4 liters, for example ("required suction volume").

In order to achieve the required suction volume a given underpressure of 4 kPa is applied to the apparatus. The magnitude of the flow volume depends to a great extent on the construction of the apparatus and its components, resulting a particular flow resistance. From the flow volume it is then possible to calculate how long the defined underpressure has to be applied (e.g. how long the magnetic valve in FIGS. 1 or 2 has to be opened) in order to achieve a flow volume of 4 liters in a measuring operation with an attached inhaler ("suction time"; for details see below). Thus, the accuracy of the measurements depends among other things on precisely monitoring the suction time and accurately determining the flow volume. With regard to this latter parameter, the USP/EP lay down the following conditions: the USP specifies a range of ±5% for delivery for a flow volume of 4 l, the flow volume (Q) and the time. In the aerodynamic particle size distribution (PSD) only ±5% is demanded for the time. The EP allows a tolerance of ±5% in the delivery of a flow volume of not more than 100 liters. As for the PSD, a tolerance of ±5% is demanded for the flow volume (Q) and the time.

Apparatus which are suitable for measurements in accordance with the conditions of the EP/USP were not available on the market at the time of the invention. Attempts to produce measuring equipment in-house on the basis of the schematic drawings contained in the EP/USP were initially unsuccessful. In particular, it was found to be impossible to achieve a sufficiently constant flow volume with the apparatus constructed as shown in FIGS. 1 and 2 (internal prior art).

Moreover, the experiments described above showed that whenever the amounts of powder delivered into the collecting tube as samples were small. (e.g. in the range from 4 to 5 µg), there were considerable fluctuations in the subsequent quantitative measurement of the contents of the collecting tube. This was attributable to the fact that powder had penetrated into the area marked P1 in FIG. 1 (connecting point for a pressure gauge) and therefore was not included in the quantitative measurement of the contents of the collecting tube.

BRIEF SUMMARY OF THE INVENTION

Therefore, one objective of the invention is to provide an apparatus by means of which the measurements prescribed by EP/USP for determining the uniformity of a dosage of drug delivered from a powder inhaler or for determining the distribution of the aerodynamic fine fraction of this dose can be carried out with the required accuracy.

A further aim of the invention is to provide a collecting tube and a process using a collecting tube of this kind by means of which the disadvantage described above, namely falsification of the measurements by quantities of powder caught up in the connecting region P1, can be avoided.

These objectives are achieved by means of a control unit according to claims 1 to 5 and collecting tubes according to claims 6 or 7 for use in an apparatus according to EP/USP and a process according to claim 9.

The control unit for flow regulation is based on the fundamental structure shown in FIGS. 1 and 2 and prescribed by EP/USP and thus contains a magnetic valve (E) controllable by a time switch (G: the letters refer to FIG. 1), preferably a two-way magnetic valve, the time switch (G), a throughflow control valve (H) connected to the magnetic valve (E) through a tubular or pipe-shaped connecting member, a suction device, preferably a vacuum pump (F) which is connected to the valve (E), and a connector (D) which leads from the throughflow control valve (H) through the filter (B) to the collecting tube (A) or to the impactor (FIG. 2). According to one embodiment of the invention the control unit also contains means for measuring the air flow volume, these means being adapted to be calibrated for measuring the air flow volume and preferably being a calibratable mechanical or electrical flywheel flow sensor.

The inventor has also discovered that a particularly uniform flow volume can be achieved if a damping filter is mounted at the entry section of the flow sensor (or the intake tube formed thereon).

It has been found that by using the calibratable sensor, optionally in conjunction with a damping filter placed accordingly in the entry section, fluctuations in flow shown on the display can be reduced from about 2 I to 0.1, or at most 0.2 I.

In another embodiment of the invention the control unit contains two vacuum measuring devices for measuring the underpressure at each side of the throughflow control valve (connecting points P2 and P3 in FIG. 1 and FIG. 2). The air supplied to the vacuum measuring devices is provided through a capillary, in each case, encased in a stable outer tube. This tube acts on the one hand as a support for the vacuum measuring device and secondly as a protection for the capillary.

Preferably, the control unit contains a control device through which the valve opening is controlled by the time switch. Preferably, also, the display of the measuring device for the flywheel flow sensor is integrated in the housing of the control device.

Preferably, also, at least the magnetic valve, the throughflow control valve and the throughflow sensor are mounted on the same baseplate.

The valve control using the control device makes it possible to adjust the opening of the valve. The duration of opening of the valve can be varied in a delivery process. The flow measuring point incorporated (flywheel flow sensor) serves to monitor the flow. The constructive design of the control unit according to the invention ensures that the same amount of air is sucked in reproducibly in each test and there are no great pressure fluctuations.

The invention further provides a collecting tube for use on a control unit according to one of claims 1 to 5 in the form of a hollow cylinder, characterised in that the inner surface of the collecting tube has a peak-to-valley height of not more than 6.3. The peak-to-valley height is achieved by the use of special rotary tools (cutting plates). The manufacturer of the material and tools prescribes a certain cutting values by way of a guide for achieving the desired peak-to-valley height.

The collecting tube according to the invention also has on one side two notches, each for accommodating an O-ring, and is conical in shape on its other side at the suction end. The conical design provides bilateral pressure on the sealing ring when the lower part is screwed on. This virtually prevents secondary air from being sucked in through the thread.

The invention also relates to an apparatus for flow regulation according to EP/USP, which comprises a control unit as described above, a vacuum pump and either a measuring or dose collecting tube or a cascade impactor.

Finally, the invention provides a process for determining the uniformity of a dose of drug delivered from a powder inhaler, wherein in a first step, using a measuring collecting tube, the suction time taken to achieve the required suction volume is determined using the device according to the invention and in a second step, using a dose collecting tube, in the suction time measured, powder is delivered into the dose collecting tube from a powder inhaler mounted on the dose collecting tube.

BRIEF DESRCIPTION OF THE DRAWINGS

The invention is hereinafter explained more fully with reference to the drawings, wherein:

FIGS. 3A-3F show views of the apparatus according to the invention consisting of a control unit for regulating flow with an attached suction device and measuring/dose collecting tubes with associated parts and three sectional diagrams and views of individual components (FIGS. 3C-3F) of the apparatus;

FIGS. 6A and 6B show a dose collecting tube in longitudinal and cross section orientations, respectively;

FIGS. 6C and 6D show a measuring collecting tube in longitudinal and cross section orientations, respectively.

DETAILED DESCRIPTION OF THE INVENTION

The dimensions and tolerances specified in some of the drawings are to be regarded as examples of particularly preferred embodiments and should not be interpreted as restricting the scope of protection.

Figure 1:
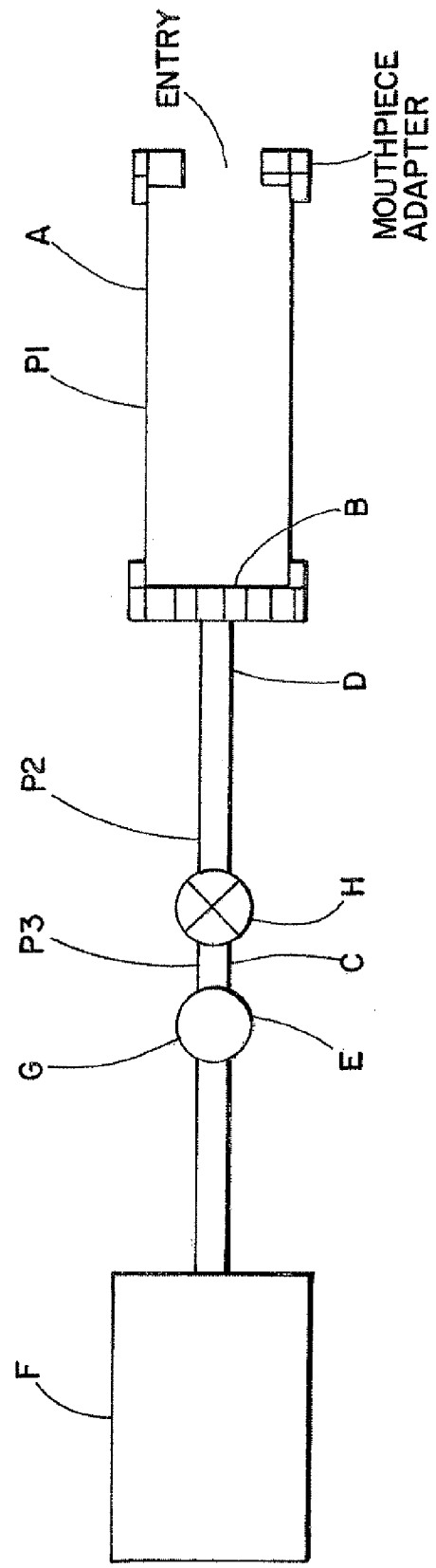
FIG. 1 shows a diagram of an apparatus for determining the quantity of active substance delivered in accordance with the European Pharmacopoeia, 3rd Edition, Supplement 2000.
Figure 2:
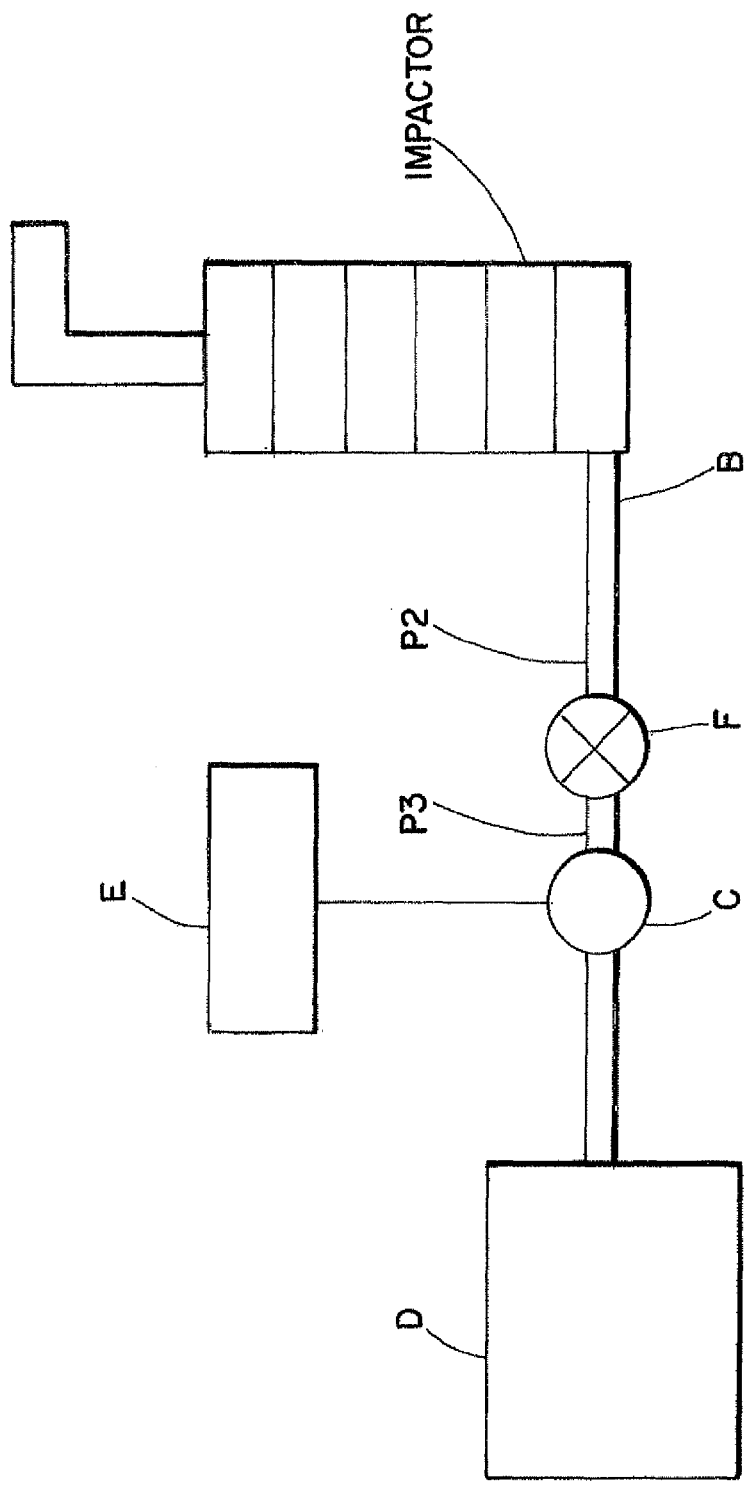
FIG. 2 shows a diagram of an apparatus for determining the aerodynamic particle size according to the European Pharmacopoeia, 3rd Edition, Supplement 2000.

FIGS. 1 and 2 are illustrations from the European Pharmacopoeia, Supplement 2000, and diagrammatically show the basic structure of apparatus for determining the uniformity of the dosage delivered by powder inhalers or for determining the aerodynamic particle size.

An underpressure is produced by means of a vacuum pump. The flow volume in the collecting tube or in the impactor is controlled by means of a two-way magnetic valve and a throughflow control valve. The vacuum pump, valves and collecting tube or impactor are joined together by connecting tubes or connectors. The two-way valve is controlled by a time switch. "P1", "P2" and "P3" denote the points where pressure measurements may be taken.

Specifically, FIG. 1 shows the following components: The pump F is connected to the magnetic valve by a short and/or wide vacuum tube (internal diameter $Di \geqq 10$ mm) and connectors. The two-way valve E opens with little air resistance and must have a Di of $\geqq 8$ mm and a maximum response time of 100 ms. The magnetic valve E may be opened for the required length of time by means of a time switch G and is connected to a throughflow control valve H via a connector C ($Di \geqq 8$ mm; e.g. a short metal connection with a small-diameter branch to measuring point P3). The throughflow control valve H is a regulating valve with a Cv value ≧1. This is followed by a short metal connection with a small diameter branch to measuring point P2. The collecting tube or the impactor is connected to the control unit by a vacuum tube D with Di=8+/−0.5 mm and a length L=50+/−10 cm. In order to adjust the underpressure, a vacuum tube at P1 on the collecting tube A should be connected to a manometer. The flow volume applied can be measured by a connection (adapter/silicon tube) at the entrance to the collecting tube A to the flywheel flow sensor. According to the figure shown, the collecting tube should have an internal diameter of 34.85 mm and a length of 12 cm. On its back wall at the suction end, the collecting tube A is provided with a filter B, e.g. a fibreglass filter. At the pressure measuring points P3 and P2 provided at the suction end or at the collecting tube end, the absolute pressure is measured while at P1 the differential pressure relative to atmospheric pressure is measured.

In FIG. 2 the vacuum pump is designated D, the magnetic valve C, the time switch E, the connector A, the throughflow control valve F and the connecting tube B. Instead of the collecting tube A in FIG. 1 an impactor is attached to the connecting tube B.

The method of operation of the apparatus shown in FIGS. 1 and 2 is explained in the introduction.

Figure 3A:
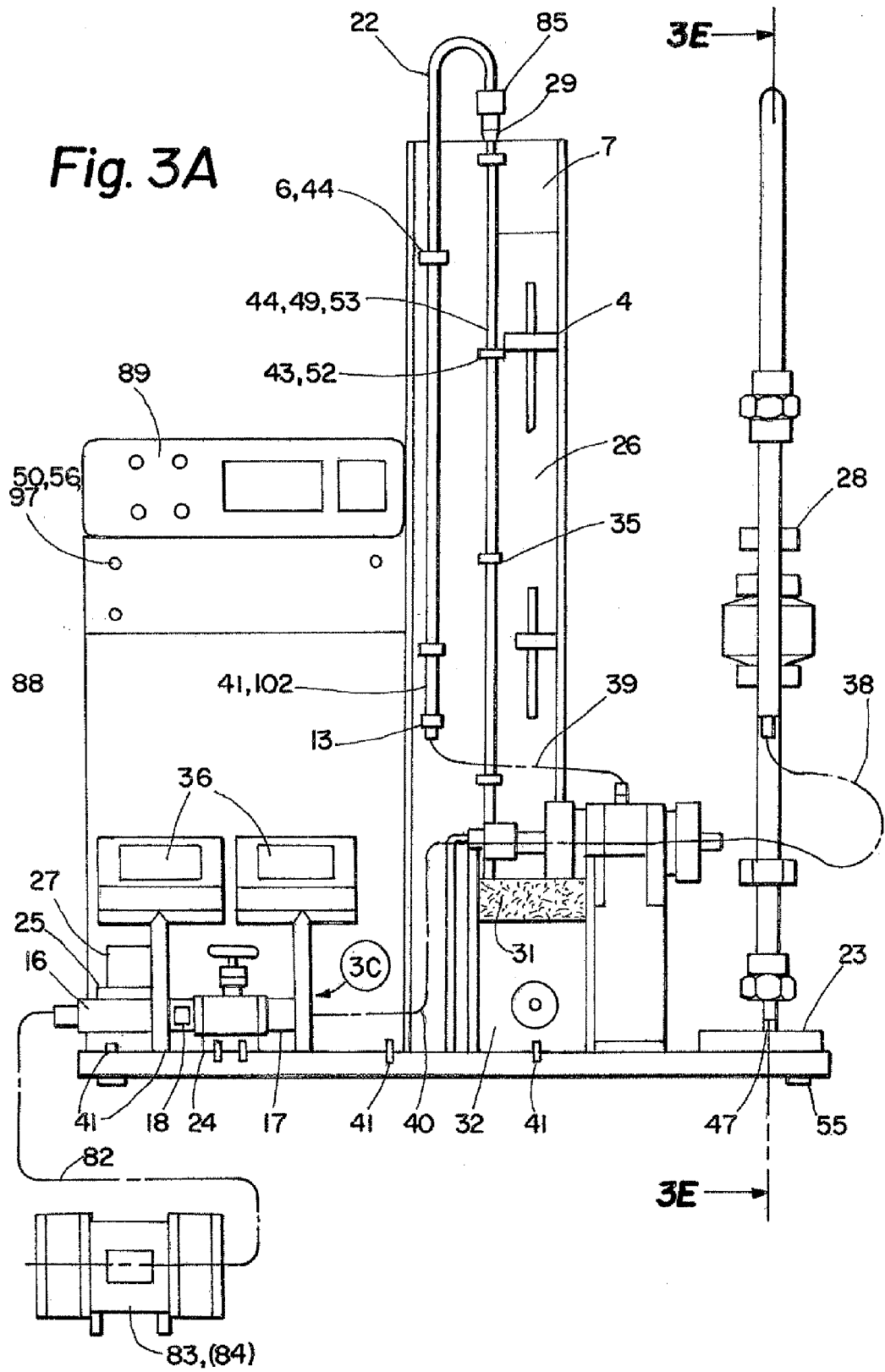

FIGS. 3A and 3F show an apparatus according to the invention with a control unit according to the invention, a suction device 83 attached thereto (e.g. a vacuum pump 84) and a measuring collecting tube connected to the control unit via the tube connection 40. (The tube connection 39 is produced to set the drop in pressure while the tube connection 38 is provided for determining the flow volume applied). To the right hand side of the apparatus (FIG. 3E) are provided a measuring collecting tube 68 and a dose collecting tube 60 with additional connecting parts. The sectional drawings show a collecting tube holder (FIG. 3D) or a flywheel measuring sensor with connecting parts (FIGS. 3E and F). FIG. 3C shows a vacuum measuring device with connecting parts in side view.

Attached to the control unit is a suction device 83, e.g. a vacuum pump 84, for generating the necessary suction. In order to be able to operate the control unit with the least possible variation in flow, a corresponding suction volume is required. The prerequisite for this is therefore a suitable vacuum pump with sufficient suction capacity. The vacuum pump ME16 or the chemically resistant pump ME16C made by Messrs Vacuubrand GmbH of Wertheim are suitable, for example. The choice depends of the particular load imposed by the suction of gases or solvent vapours. This pump is a one-step dry-compressing diaphragm vacuum pump. By exchanging the individual pump heads a suction capacity of up to 10.1 m$^3$/h is achieved. In this pump the flutter valves are opened and closed automatically by the gas flow. If a relief vacuum is attached to the outlet connector for sucking out harmful gases or solvent vapours, care must be taken to ensure that this is not applied when the pump is not operating as this might damage the flutter valves. The pump achieves full suction capacity and final pressure only once the operating temperature has been reached. This generally takes about 15 minutes. A minimum preheating time of 15 minutes must therefore be allowed. The manufacturer's operating instructions should be followed.

Alternatively, other suction devices may be used provided that the necessary "critical throughflow" (see below) is achieved.

The vacuum is connected by a vacuum tube 82, e.g. a dimensionally stable rubber vacuum tube (DN 20, $D_a$=45 mm,1 $d_i$=19 mm) to the control unit.

The control unit itself consists of a number of individual parts:

A magnetic valve 27 controlled by a timer serves to switch a defined suction volume through the inhaler and the dose collecting tube (or cascade impactor) over a given time at a constant flow volume. A suitable magnetic valve may be, for example, the one made by Messrs Bürkert of Filderstadt (Order No. 062347 E). The housing part is made of stainless steel (1.4581), the switching times for opening are between 10 and 20 ms and for closing between 20 and 30 ms, the nominal width is 10 mm, the $C_v$ is 1.5 m$^3$/h (water). The voltage is 24 V and the frequency 50 Hz.

However, all other valves which meet the requirements and terms of the USP/EP are also suitable, i.e. if they have an internal diameter greater than or equal to 8 mm and a maximum response time of less than 100 ms.

Figure 3B:
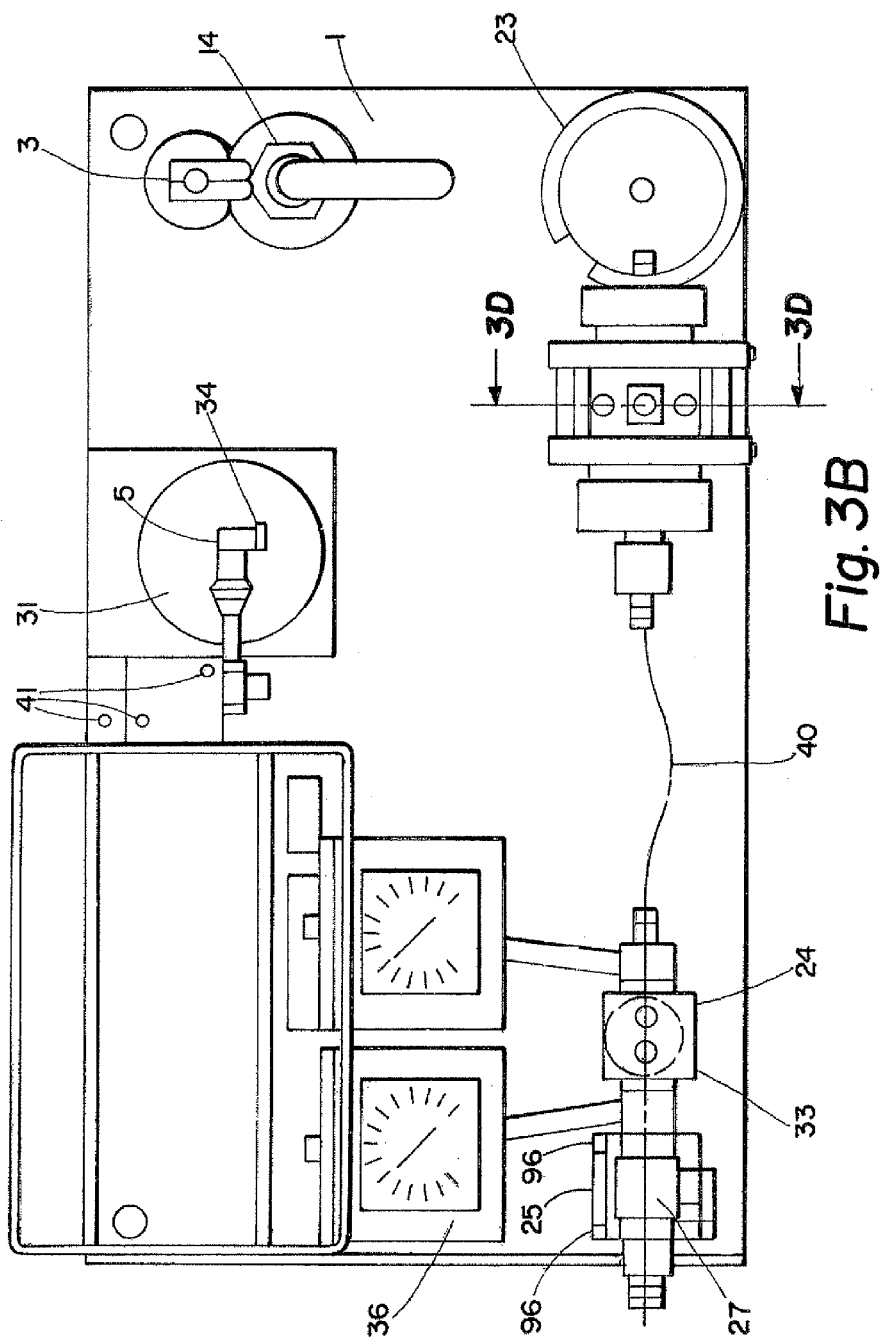
Figure 3C:
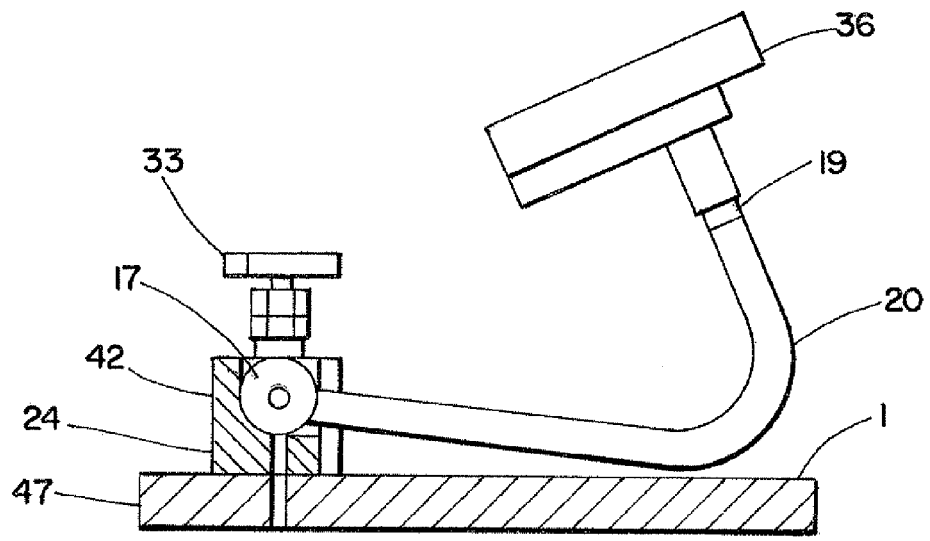

Also shown in FIGS. 3A and 3B in connection with the valve 27 are a retaining angle bracket 25 and a tube dropper 16 for the valve 27 and fixing means 41 and 96.

A throughflow control valve 33 with regulating stopcock is used to manually set the required drop in pressure. With this throughflow control valve 33—when the magnetic valve 27 is open—a defined drop in pressure is obtained, particularly a drop in pressure of 4.0 kPa (as prescribed by EP/USP). When converted this corresponds to 40.8 cm of water column, read off on the scale 26 of the manometer 22, 29. As will be explained in more detail hereinafter, the underpressure applied is adjusted using a measuring collecting tube 68 and a differential pressure measuring instrument (manometer) 22, 29 connected thereto.

The throughflow control valve 33 used may be, for example, a fine regulating needle valve made by Messrs Hoke mbH of 60314 Frankfurt, which has a $C_v$ factor of 1.2. However, other valves are also suitable provided that they guarantee the $C_v$ value of more than 1 which is required according to the EP/USP.

Also shown is a holder 24 for the throughflow control valve 33.

On both sides of the throughflow control valve 33 is a connector 18 (in this case with a double nipple) or 17 (in this case with a tube liner) for a pressure/vacuum measuring device 36. The absolute pressure on both sides of the throughflow control valve 33 is measured by means of these pressure/vacuum measuring devices 36 mounted adjacent to the throughflow control valve. If the pressure ratio between the pressure measuring points P3 and P2 (cf. FIG. 1 and FIG. 2) is less than or equal to 0.5 the requirement for "critical throughflow" according to USP/EP is met. Once the flow is applied, at least this value must be maintained. If it is not achieved a more powerful suction unit must be attached.

The fully electronic vacuum measuring devices made by Messrs Vacuubrand of Wertheim may be used, for example, as the pressure/vacuum measuring devices 36. According to the manufacturer the devices have a measuring range from 1 to 1080 mbar (measuring accuracy ≦±1 mbar after calibration and at constant temperature).

Moreover, the control unit contains a control device 89. This contains a connecting bushing for the two-way magnetic valve 27, optionally with an indicator light, a timer (preferably a digital timer), hereinafter also referred to as a "timer" or "time switch", for controlling the two way magnetic valve 27, and an initiator for starting the timer (e.g. a start key). The timer is preferably suitable for measurements with an adjustment range from 0.001 s to 9999 h, for example (accuracy of setting during measurement to two decimal places, tolerance limit ±0.3 s in a calibrating range from 5 to 7 s). Optionally, the control device 89 also comprises a mains indicator light, a connecting bushing for the flywheel flow sensor 37, an indicator for the throughflow at the flywheel flow sensor 37 and a (tilt) switch for continuous or intermittent operation of the magnetic valve 27, as desired.

The control device 89 is preferably firmly attached to the other components of the control unit by means of a retaining plate 88 and the baseplate 1. This is advantageous as the control unit and flywheel flow sensor have to be calibrated as a coherent unit. Firmly joining the components together ensures that the individual parts are associated with one another. Reference numerals 41, 50, 56, 97 and 102 denote parts of fixing means (e.g. 41 and 56: countersunk flange-head screw with hexagonal recess; 50: washer; 97: cap nut; 102: hexagonal nut).

The manometer consisting of 22, 29, 7, 26 and various other parts is constructed as a differential pressure measuring gauge and serves to indicate and adjust the given pressure drop (4.0 kPa). The pressure drop is always adjusted in conjunction with the device in question (e.g. the "HandiHaler®" 80 inhaler) or a suitable equivalent resistor 66 which simulates the flow resistance, e.g. the HandiHaler® 80 inhaler with capsule placed therein. The manometer consists, for example, as shown in FIG. 3, of a metal tube 22, a glass riser pipe 29 with a moveable scale 26 (e.g. 50 cm) for measuring the water column. The riser pipe 29 is immersed in a vessel 31 filled with water, the diameter of which should be at least 20 times the internal diameter of the riser pipe 29 (e.g. a crystallising dish). To improve the wetting of the riser pipe 29 a few drops of rinse agent are added to the water. A metal tube with olive 13 is firmly screwed to the riser pipe 29. The riser pipe 29 (glass tube) is supplied by the manufacturer together with a sealing ring which is intended to tighten as the screw is turned and thereby tightly connect the glass tube to the metal tube. However, it has been found that a connection of this kind does nor produce an adequate seal and moreover when the original seal is tightened the glass tube can easily break apart at the thread. Instead it has proved beneficial to solder a small flange onto the metal tube and place an O-ring thereon such that when the screw is tightened the glass tube is sealed against the flange at the top edge.

During measurement of the drop in pressure in the measuring collecting tube 68, the measuring collecting tube 68 is connected to the connector 69 (position P1 in FIG. 1) at the metal olive 13 by means of the vacuum tube 39 (e.g. Di=8 mm, L=35 cm). During measurement care must be taken to ensure that the vessel 31 is filled with sufficient water (adjustable in height by means of the device 32, e.g. a laboratory stand). The riser pipe 29 must dip into the water and the zero point of the scale 26 (which is optionally cut off at the zero point) is adjusted by moving it to the level of the lower meniscus in the riser pipe or device 32. The scale 26 can be adjusted by removing and reattaching the fixing means.

FIG. 3A also shows a plurality of holders 35 for the manometer (consisting of 22, 29, 7, 26 and various other parts), provided with fixing means 43 and 52 (e.g. a countersunk screw and hexagonal nut), and scale holders 4 with a disc 49 on the scale holder and fixing means 44 and 53 (e.g. countersunk screw and self-locking hexagonal nut), an O-ring 85, holder 6 with fixing means 44, milled hollow nuts 34 for the scale holder, spacers 5, a mounting plate 7 and other fixing means 41.

As already mentioned the manometer consisting of 22, 29, 7, 26 etc may be used together with the measuring collecting tube 68.

The flywheel flow sensor 37 is used to measure and control the flow volume which has been adjusted or is to be adjusted. The sensor 37 is smoothly connected to a suction tube 14 by means of a tube connecting section 15 and a seal 93 and this suction tube 14 has at its end a threaded sleeve 92 and a tube connector 30 (e.g. G⅜ ⅓ screw). In order to be able to measure the flow volume precisely, the flywheel flow sensor must be able to be calibrated and adjusted.

The measuring range (air/gas) of the flywheel flow sensor is between 0.4 and 20 m/s, the temperature resistance is from −20° C. to +100° C. The measurements are taken for example at five different values (28.3, 35.0, 39.0, 45.0 and 50.0 l/min). The tolerance specified is ±1 l/min while the warning limit specified is 0.8 l/min. Previous test reports from practice have shown that the error/deviations are at ±0.1 to a maximum of 0.4 l/min.

Flowmeters used in the prior art show deviations of at least 2%, i.e. 2.4 liters per minute (brochure produced by Messrs Copley). By contrast, with the flywheel flow sensor used according to the invention in conjunction with the control unit, maximum deviations of 0.7 l/min and generally only deviations of 0.1 to 0.4 l/min can be expected. This substantially improves the accuracy of measurement.

The flywheel flow sensor 37 and the suction tube 14 are joined together by means of a holder 8, a threaded bolt 9, a threaded pin for suction tube holders 48 and a screw-type pipe clamp 28 with a stand 2, anchored on the baseplate 1 by means of a footplate 3. Reference numeral 47 denotes a fixing means, e.g. a countersunk screw. The suction tube has specific dimensions at the entry and exit sections to smooth out any turbulence formed in the air current. In particular, the transition from the suction tube to the flywheel flow sensor is constructed so that there is no tapering in cross section and there is only a small seam in the connector. This prevents flow turbulence from occurring in front of the flywheel.

The construction of the flywheel flow sensor and the adjacent tubes and connections is achieved by always measuring the flow at the same defined point. The accuracy of measurement and reliability are increased by defined entry and exit sections.

Optionally, a protective grid may be mounted on the suction tube to prevent smaller lightweight objects from being pulled into the suction tube. However, it is then necessary to check the extent to which the airflow is affected by a grid of this kind. According to the invention it has nevertheless proved particularly beneficial to mount a damping filter secured in a Delrin gasket (104, 105) and screwed to a check nut. This ensures that the indication of flow, which may fluctuate by 2 l/min, for example, where no damping filter is used, is subject to a fluctuation of only 0.1 up to a maximum of 0.2 l/min with the damping filter. The flywheel flow sensor 37 is used in conjunction with a measuring collecting tube 68 and is attached thereto via an adapter 64 through a tube 38, e.g. made of silicon with Di=12×2.5 mm and L=50 cm.

In the embodiment of the apparatus according to the invention shown in FIG. 3E, the control unit is either connected to a measuring collecting tube 68—in order to adjust the suction—or to a dose collecting tube 68—in order to carry out the actual measurement, i.e. determine the test point "dosage delivered/quantity of active substance". In both cases the collecting tube is connected to the throughflow control valve 33 and the vacuum measuring device connection 17 by means of a vacuum tube 40 made of rubber, for example.

Measuring Collecting Tube:

The measuring collecting tube 68 serves to adjust the suction and determine the resulting flow volume. From this the time taken for the necessary flow volume, e.g. 4 liters, is calculated. This is done using the differential pressure measuring instrument/manometer 22, 29 etc., a suitable equivalent resistor 66 and the flywheel flow sensor 37. The measuring collecting tube 68 has the same dimensions as the dose collecting tube 60 but differs from it by the presence of a connecting olive 69 at the connecting point P1 (FIG. 1). By means of this, in order to adjust the drop in pressure, the measuring collecting tube is connected to the manometer 22, 29 etc., at the tube liner 13, via a vacuum tube 39 made of rubber, for example, and having the dimensions Di=8 mm, L=35 cm.

The connecting olive is preferably pressed into the measuring collecting tube so as to obtain the diameter of 2.2 mm specified in USP/EP right through to the interior of the collecting tube. With larger apertures (e.g. 8-10 mm) the air current in the collecting tube may be disturbed by turbulence, leading to significant fluctuations in the pressure to be read off on the manometer.

A perforated plate 57 for supporting the fibreglass filter 95 is placed in the lower part of the collecting tube (in both the measuring and dose collecting tubes). The open-pored side of the perforated plate 57 should be mounted facing upwards and the "hole side" (the smooth side of the perforated plate, the suction side) should be placed downwardly. If the perforated plate 57 is inserted the wrong way round this results in a significant increase in the flow resistance. By virtue of its construction the perforated plate ensures uniform suction over the entire fibreglass filter. Tearing in the centre of the filter caused by suction effects as observed with tubes supplied by other manufacturers is eliminated.

The fibreglass filter 95 and an O-ring 70 are positioned on the perforated plate 57. The O-ring 70 serves to hold the filter 95 and seal off the screwed-on lower part 61 with the collecting tube 60 or 68. Because of the cone applied underneath the thread of the collecting tube 60 or 68 the filter is pressed through the O-ring on to the perforated screen and at the same time laterally seals off the thread at the bottom. If the parts have been correctly assembled it is impossible for any "secondary air" to be drawn in. When the collecting tube is inserted, the lower part 61 (with O-rings 86) is connected to the control unit on the suction side by means of the connecting adapter 68 (internal diameter 8 mm at its narrowest point, for example) through the vacuum tube 40 (length about 45 cm, Di=8.0 mm±0.5 mm).

As shown in FIGS. 6A and 6C, two O-rings 71 which provide a seal and firm fit are located at the sample entry end of the collecting tube. Adjoining them is optionally a collecting tube adapter 62 or an equivalent resistor 67 which is either designed for the corresponding inhaler device (e.g. the Handi-Haler 80® (collecting tube adapter 62) or is provided with an integrated suitable equivalent resistor 66 (collecting tube adapter 67) which simulates the flow resistance, e.g. the HandiHaler 80 inhaler with capsule inserted. Adjustment of the underpressure with the inhaler and the capsule inserted as proposed in EP/USP is not possible in the case of the Handi-Haler owing to the vibration of the capsule. The column of water would fluctuate too much and could not be adjusted to precisely 40.8 cm. The device or the equivalent resistor crucially influence the required underpressure which is to be adjusted and the resulting flow adjustment for later measurement. The construction of the required inhaler adapter 62 for the collecting tube and the adapter 67 with an integrated equivalent resistor 66 depends on the type of inhaler used (for more information see below). The use of two O-rings mounted one behind the other increases the leaktight seal and firm fit. If only one O-ring is used the connection to the adapter is less stable and becomes leaky more easily.

FIGS. 6A and 6C also show the conically extending suction end of the collecting tube which is tightly connected to the lower part 61 by means of a silicon ring. The cone presses the inserted silicon ring against the wall and the filter, thereby preventing "secondary air" from being sucked in through the thread or screw fitting.

Also shown are the closure cap 59 for the collecting tube and the protective cap 65 for the equivalent resistor 66.

Dose Collecting Tube:

For the job of determining the "uniformity of the dosage delivered" in the case of inhalable powders the dose collecting tube 60 is an essential aid. It serves to receive the quantity of powder delivered from the inhaler device or from the powder capsule contained therein. The dose collecting tube 60 is made of plastics (Delrin) for example and has in particular the internal length of 120 mm which is precisely prescribed by EP/USP and an internal diameter of 34.85 mm. Typically, a number of dose collecting tubes are supplied. These can then be individually marked for identification and accurate fit. Other materials, such as Teflon, for example, may also be used to produce the collecting tubes. The disadvantage would be the higher price of the material, its poor "machineability" and the difficulty of processing the surface within the collecting tube. In view of the stringent requirements as to accuracy of fit and leaktightness, Teflon connections are "harder to operate". If Teflon has to be used, joints which comprise a combination of Delrin and Teflon are preferred as the "soft" Delrin makes the Teflon "easier to operate". Alternatively, other materials may also be used. However, these should also be checked for compatibility with the active substances to be measured and solvent used.

The porosity of the fibreglass filters 95 used has a crucial influence on the retention of the active substance and affects the flow resistance of the dose collecting tube 68 and hence also the operating parameters of the control unit. In particular, the effects on the necessary suction of the suction unit should be borne in mind.

Figure 7A:
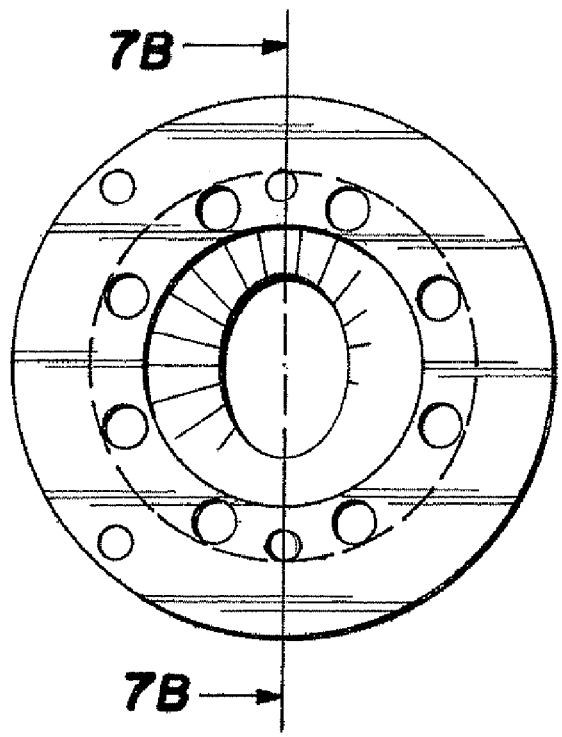
FIGS. 7A and 7B show an adapter for connecting the inhaler to the dose collecting tube in cross section and longitudinal orientations, respectively.
Figure 7B:
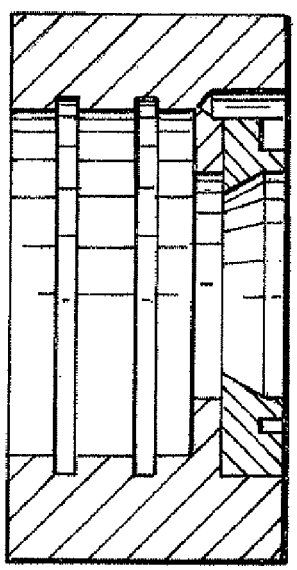

The closure member at the suction side of the dose collecting tube 60 has the same structure as that of the measuring collecting tube. The dimensions of the dose collecting tube 60 correspond to those of the measuring collecting tube 68. However, the dose collecting tube 60 has no connecting olive for the manometer P1, thus preventing quantities of the powder introduced from being trapped at a connecting point of this kind and then not picked up in the quantitative measurement of the amount of powder introduced. The entry to the dose collecting tube 60 (with O-ring 71) is provided with an inhaler adapter 62, during the delivery process, which serves to accommodate the particular type of inhaler and is adapted thereto. The adapter 62 is supposed to ensure a tension-free tight fit. In the case of the HandiHaler inhaler, for example, it must be ensured that as a rule the silicon mass is no thicker than 7±1 mm to ensure an accurate fit and seal. As shown in FIGS. 7A and 7B the adapter 62 is provided with an insert formed therein during casting, which ensures that the front of the inhaler mouthpiece ends in the same plane as the dose collecting tube and adjoins the mouthpiece in a fully leaktight manner. The silicon insert itself is secured by bead-like shapes in the adapter profile and is thus fixed in the cover. This is achieved by means of 5 mm boreholes in the adapter. The silicon mass sets in the bores and once cured secures the insert against rotation.

FIG. 3E also shows an angle bracket 94 for the inhaler adapter 62 (with fixing means 98), a blind stopper 63 which serves to seal off the collecting tubes during the processing of the sample, and the HandiHaler® 80 inhaler with a support pin 99 for stably securing the HandiHaler® 80 to the inhaler adapter 62. Other inhalers may also be used. In this case collecting tube adapters designed to fit these other inhalers should be used. The measuring and dose collecting tubes and the adapter are preferably made of Delrin® (also known as polydelrin or POM). Delrin® is a polyoxymethylene (POM) and is an alternative to Teflon® which is mentioned as a material in the Pharmacopoeia. Finally, the material should be selected as a function of the active substance which is to be measured: any chance of interaction between the material and the active substance must be ruled out. Therefore, for each active substance, compatibility with the above mentioned manufacturing material must be verified. Other materials are also possible for the collecting tubes provided that first of all the dimensions and requirements laid down in the EP/USP are complied with and secondly compatibility with the active substances is ensured. If organic solvents are used, e.g. mixtures of methanol and water, the material must also be tested for suitability and material compatibility with these materials.

In the manufacture of a collecting tube the individual parts have certain manufacturing tolerances. Therefore, all the parts of each collecting tube should be marked. Only parts which belong together should be used. If individual parts are repaired or replaced, the entire collecting tube must be included. The reason for this is that the accuracy of fit and compatibility with other adapters must be guaranteed.

It has proved advantageous within the scope of the invention to produce manufactured parts with tolerances which are smaller than those specified in DIN 7168-m. The narrower tolerances resulting from manufacture ensure a high accuracy of fit which contributes to a more constant airflow volume and hence more precise measurements.

Figure 3D:
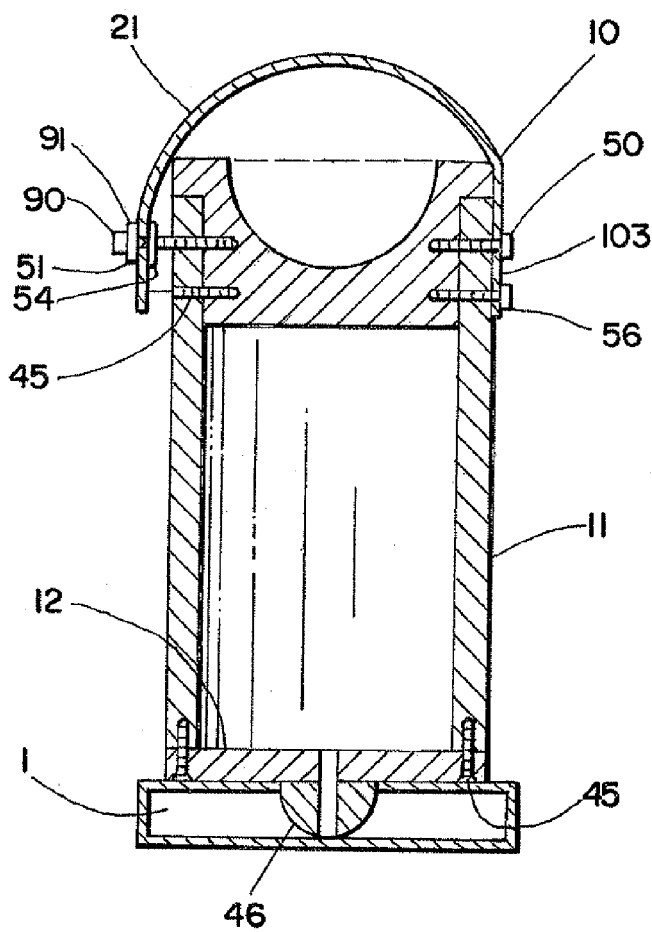

FIG. 3D shows a collecting tube holder 10 with side portions 11 and rubber bands 21 for securing the collecting tube. The rubber bands 21 are secured, for example, on one side by means of a washer 50, a fixing means 56 (e.g. a countersunk flange-head screw with hexagonal recess) and a sheet metal plate 103. On the opposite side the connection is expediently releasable, e.g. by means of cylindrical screws 90, hollow rivets 91 for the rubber band, washers 51 for the rubber band and hexagonal nuts 54. Alternatively it is possible to use a touch-and-close strip of corresponding dimensions instead of the rubber bands 21. On the opposite side the connection is expediently made using a piece of touch-and-close strip which is stuck on, for example, thereby dispensing with the cylindrical screws 90, the hollow rivets 91 for the rubber band, the washers 51 for the rubber band and the hexagonal nuts 54. The collecting tube holder 10 and side portions 11 are joined together by fixing means 45. The side portions 11 are joined to the baseplate 1 by means of a footplate 12 and fixing means 45 and 46.

Figure 8A:
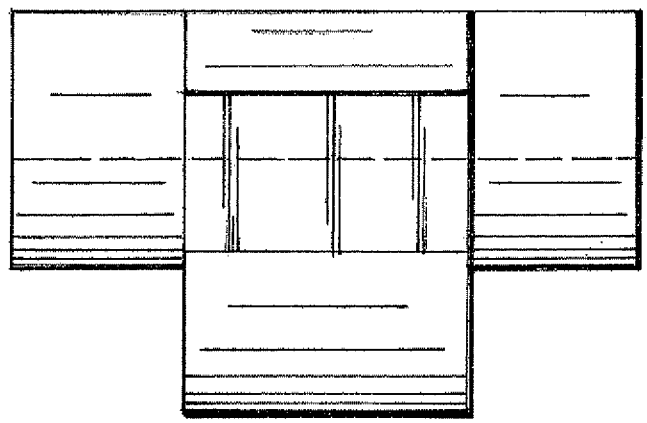
FIGS. 8A and 8B show an adapter for attaching collecting tubes of different sizes.
Figure 8B:
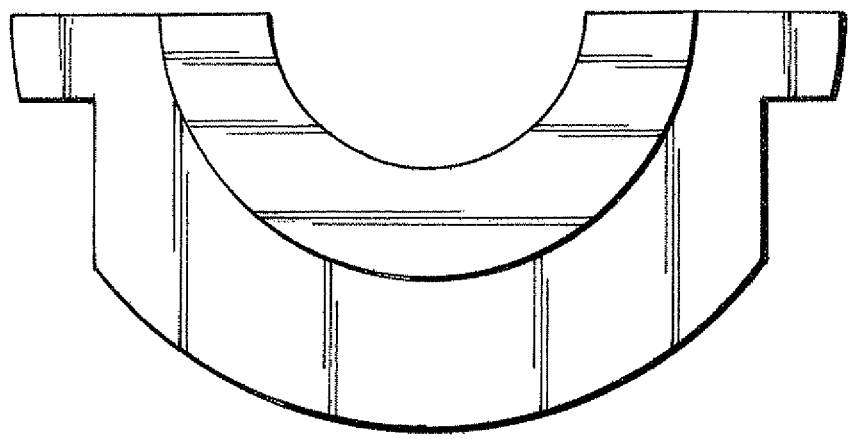

The collecting tube holder may be provided with an adapter 122 (FIGS. 8A and 8D) which makes it possible to clamp collecting tubes of different dimensions (e.g. the smaller tubes for aerosols and solutions) in the holder and operate them using the control unit according to the invention.

Figure 5:
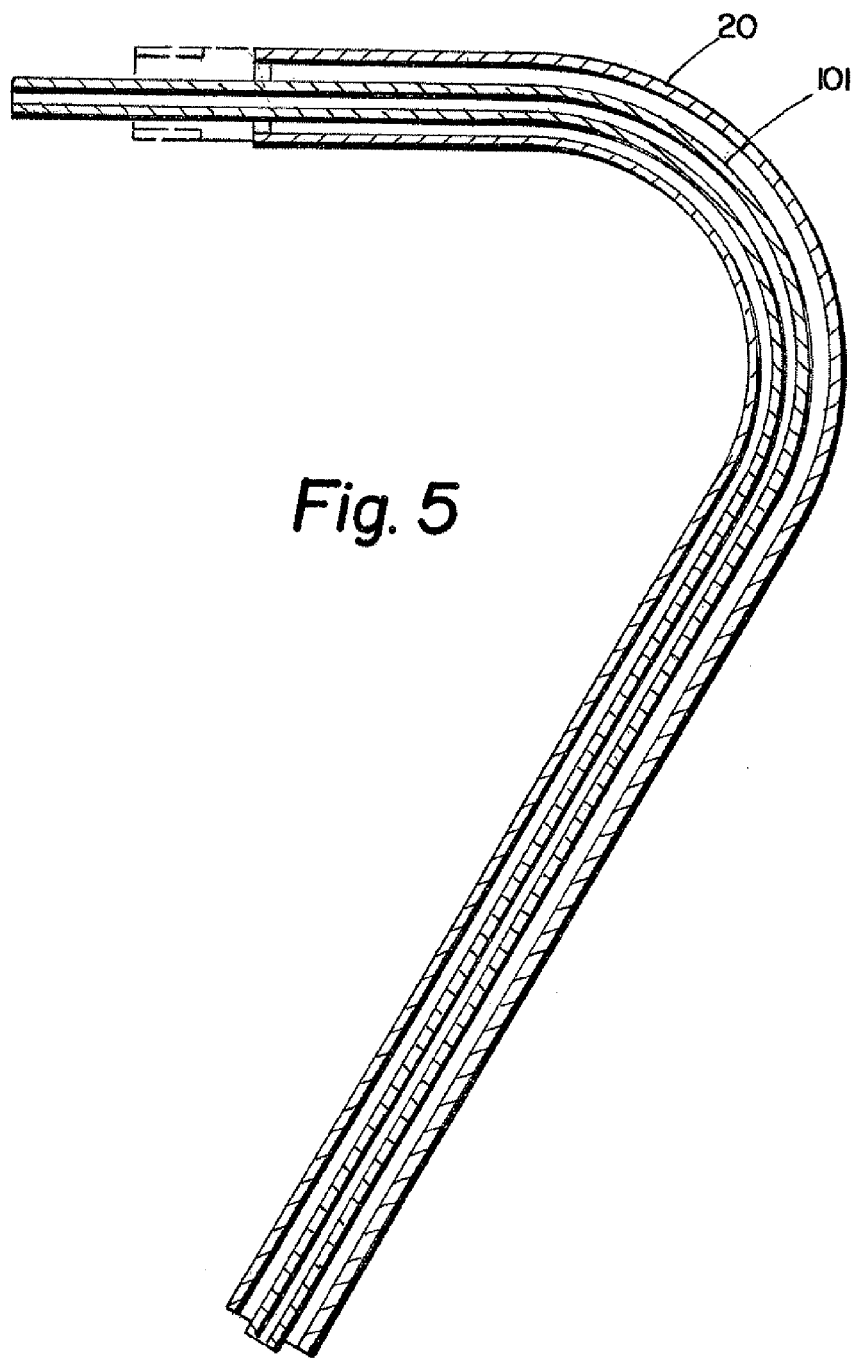
FIG. 5 shows the retaining tube mounted at P2 or P3 and leading to the vacuum measuring device, with a capillary placed therein, in section.

Finally, FIG. 3C shows a vacuum measuring device 36 connected to the vacuum measuring device attachment 17 by means of a threaded nipple 19 and a holding tube 20. As shown in FIG. 5, there is a thin capillary 101 in the holding tube 20. Leaks are prevented by soldering the tube 20 and the capillary 101 at positions 17 and 18, respectively. Moreover, the advantage of the smaller volume of the capillary contents is that when the vacuum measuring device is included in the measuring operation, the capillaries cause little or no measurable loss of volume. The small volume of air thus has no effect on the suction volume to be drawn up during measurement. The outer tube acts as a holder for the measuring device, on the one hand, and as a protection for the capillaries placed therein, on the other hand. FIG. 3 also shows the throughflow control valve 33, a threaded pin 42 for fixing the throughflow control valve, a holder 24 for the valve and fixing means 47 for attachment to the baseplate 1.

In the embodiment shown, the magnetic valve 27, the throughflow control valve 33, the collecting tube 10, 11, 12 are directly anchored on the baseplate 1 while the flywheel flow sensor 37 is anchored thereon by means of the stand 2 and the control device 89 and manometer 22, 29 are anchored thereon by means of holding plates. The baseplate contains oscillating metal buffers 55 on its underside. Finally, secured to the baseplate 1 is an impactor standing dish 23 which is used when the control unit is used with an impactor (cf. the description relating to FIG. 4). The metal construction and the fact that all the components are screwed together means that no reference earth potentials can occur. The entire control unit is earthed in itself by means of the control device and the connecting cable of the socket. Any static charges jumping over are also conducted away. Each device has an EMV certificate. The control unit is expediently designed for modern voltages (220 V and 110 V) and the electric modules are designed for the appropriate type of current. The modules on the control unit may be labelled, e.g. in German or English.

Figure 4A:
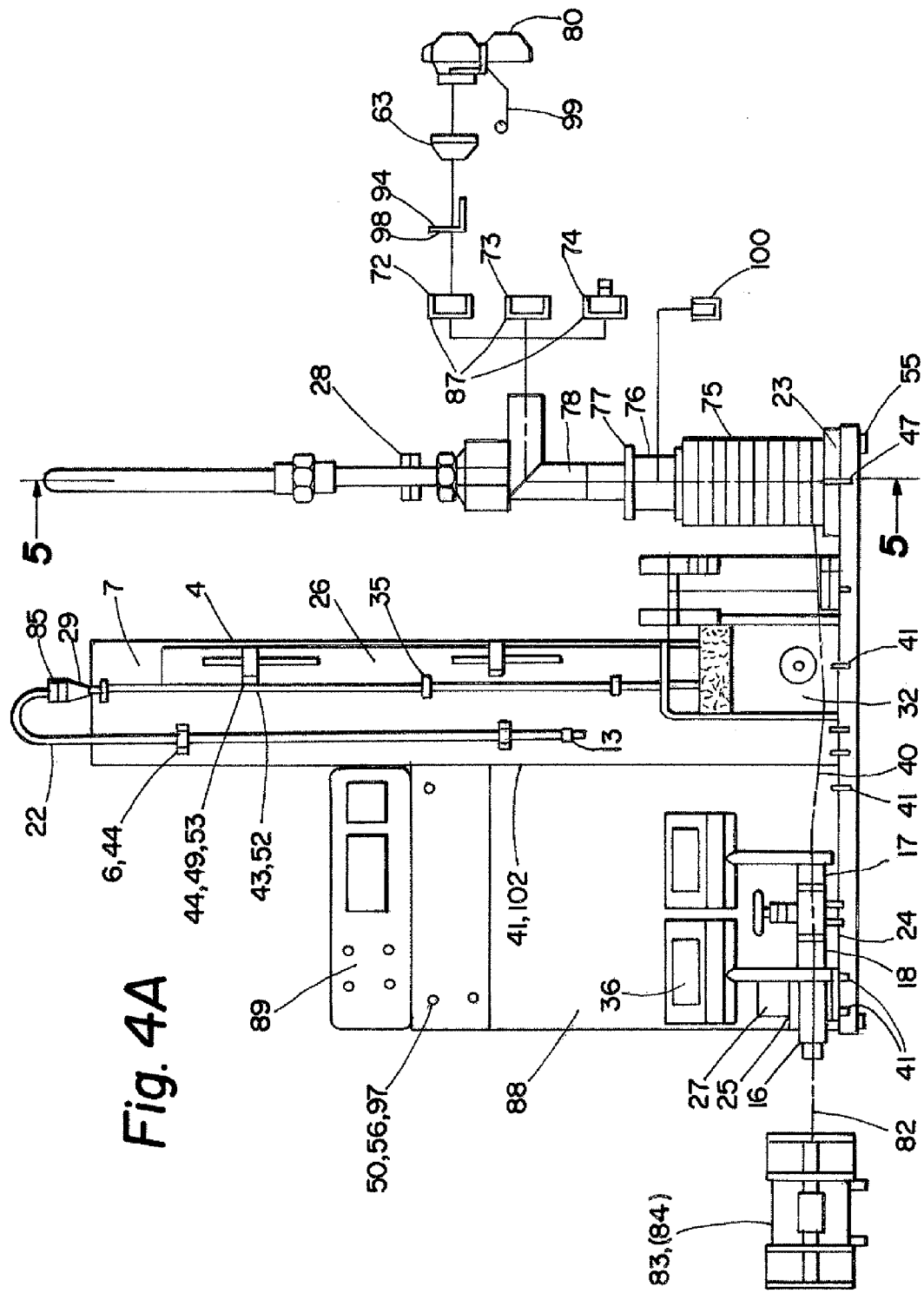
FIGS. 4A and 4B show views of the apparatus according to the invention comprising a control unit for regulating flow with an attached suction device and cascade impactor with associated parts.
Figure 4B:
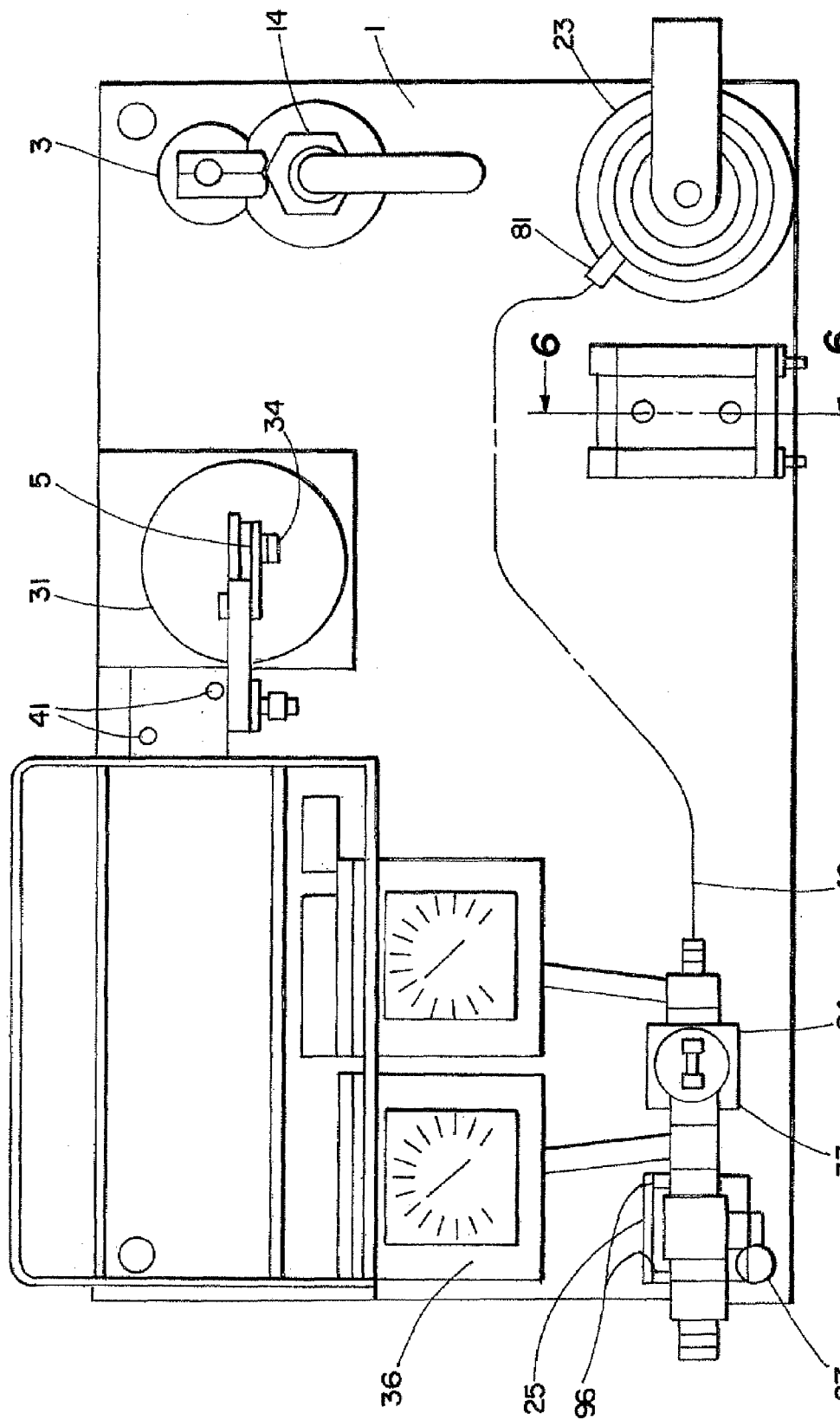

FIGS. 4A and 4B shows an apparatus according to the invention with a control unit according to the invention, a suction device 83 attached thereto (e.g. a vacuum pump 84) and a (cascade) impactor 75 attached to the control unit via the tube connection 40. On the right, next to the apparatus (FIG. 4A), are shown a HandiHaler® 80 and other attachments. Any reference numerals appearing in FIGS. 4A and 4B which have already been used in FIGS. 3A-3F have the same meanings in FIGS. 4A and 4B as in FIGS. 3A-3F and only some of them will be explained again hereinafter.

The apparatus shown is used to determine the distribution of the aerodynamic fine fraction in a dose of drug delivered from am inhaler. This is done using a (cascade) impactor 75, a suitable one being the "Andersen Cascade Impactor Mark II" with stages 0 to 7 and filters (ESM Andersen Instruments, Erlangen). This is a multi-stage multi-jet cascade impactor made up of 8 separating stages (0, 1, 2, 3, 4, 5, 6, 7, filter). For example, a binder-free boron silicate fibreglass filter with a diameter of 76 mm, a pore size of 1 µm, retaining capacity of $\geq$99.98%, 0.3 µm DOP particles at 32 l/min through 100 cm$^2$, made by Messrs Pall Gelman Sciences, 600 South Wagner Road, Ann Arbor, Mich. 481003, may be used in the impactor.

The sample inlet is a sample induction port (SIP) 78, e.g. the Andersen Induction Port USP (ESM Andersen Instruments, Erlangen). This is connected to the impactor 75 via a connecting portion "High Top USP" 77 (ESM Andersen Instruments, Erlangen) and a pre-separator 76. The pre-separator 76 serves to separate off large particles. The dimensions of the nozzle diameters of the individual separating stages are checked at regular intervals (by stage mensuration). New impactors should be measured theoretically before being used for the first time. Details of embodiments of the SIP 78 and High Top USP 77 are provided in the European Pharmacopoeia (Eur. Ph. 3, Supplement 2000).

The drawings also show an impactor standing dish 23 which is anchored to the baseplate 1 by fixing means 47 and steadies the impactor 75. On the suction side the impactor 75 is attached at its base to the control unit by means of the connecting adapter 81 and also by means of a rubber vacuum tube 40 (D=8±0.5 mm, l=450 mm). As the baseplates of the impactor are supplied from the manufacturer with plastic olives or other olives which do not meet the requirements of EP/USP of ≧8 mm±0.5, modifications are required as described.

Attachments are also shown which are to be mounted at the entry to the SIP 78, namely the inhaler adapter 72, the closure cap 73 for the SIP and the adapter 74 with olive for the SIP. O-rings are marked by reference numeral 87. The adapter 74 with olive for the SIP is used to adjust the flow and carry out measurements at the SIP (see the explanation hereinafter) and should be attached to the flywheel flow sensor 37 by means of a silicon tube (Di=12×2.5 mm, L=about 50 cm; not shown in FIG. 4). The inhaler 80 is attached to the SIP 78 via the inhaler adapter 72 for the SIP in such a way as to ensure a tension-free tight fit. This is to be ensured by suitable manufacturing measures. The closure cap 73 for the SIP is used when the cascade impactor 75 is tested for leaktightness before each measurement of the aerodynamic particle size. For this purpose the cascade impactor 75 is closed off by the closure cap 73 at the SIP 78 and a pressure of about 20 to 30 mbar below normal pressure is applied. The closure cap 73 is also used to close off the SIP during the quantitative measurement of the powder content after it has been delivered.

Finally, FIG. 4A shows the closure cap 100 for the High Top USP 77. It is used to close off the High Top USP 77 during rinsing in order to detect and quantitatively determine the active substance contained therein. The closure and protective cap 100 is provided on the inside with a silicon coating which enables the High Top to be closed off gently during the rinsing process by gentle pressure. The cap 100 also serves to protect the edges at the outlet when the device is not in use.

All the other parts bearing reference numerals have already been explained in connection with FIGS. 3A-3F.

Mode of Operation:

As explained above, the apparatus according to the invention is suitable for determining the parameters of "dose delivered" (measured using the dose collecting tube) and "distribution of the aerodynamic fine fraction" (measured using the cascade impactor). The necessary adjustment of the control unit and the method of performing the measurements will now be described in more detail.

Adjusting the Flow with the Measuring Collecting Tube:

The vacuum pump 84, the control device 89 and the two electronic vacuum measuring devices 36 are switched on. The vacuum pump 84 is brought to the required operating temperature for a minimum warm-up time of 15 minutes before the start of the flow adjustment. The manometer 22, 29 etc and the vacuum measuring devices 36 have been tested for leaktightness. This testing for leaks is an integral part of testing and maintenance for each apparatus. Theoretically it should be carried out before the control unit is operated.

The aim of adjusting the flow is to set the throughflow by means of the throughflow control valve, when a vacuum is applied to the measuring collecting tube 68, so that the drop in pressure measured at P1 (FIG. 1) within the inhaler 80 or with the equivalent resistor 66 is 4.0 kPa (40.8 cm of a column of water). According to the requirements set out in the EP/USP the pressure drop should be measured inside the inhaler. The EP/USP does not contain any more precise information. In the case of the "HandiHaler®" it has proved sensible to measure the drop in measure in the region of the mouthpiece. A suitable filter must also be selected when developing a test method. This is done as a function of the particular powder mixture. The filter should be chosen so that the powder cannot pass through it. For example, the fibreglass pre-filter GF92 (Schleicher & Schuell AG, 37582 Dassel, diameter 50 mm, Ref. No. 10421030) has proved satisfactory.

The measuring collecting tube 68 is placed on the holder 10 of the control unit and is connected at the suction end to the suction unit via an adapter 58 and a vacuum tube 40. The Pharmacopoeias (Pharm. Eur. 2000, USP 24) specify values of Di=8 mm±0.5 mm and length 50 cm±10 cm for the tube connection 40.

With capsule powder inhalers it is difficult to measure the flow in the inhalers without complex measures. Moreover, the flow through the inhaler is prone to severe fluctuations when a capsule is inserted in the inhaler. For these reasons the measuring collecting tube is generally fitted with an adapter 67 and a suitable equivalent resistor 66. The equivalent resistor 66 must have a flow resistance equal to that of the inhaler 80 complete with capsule, if the flow resistance of the inhaler 80 without a capsule is equal to the rated value. In addition, the equivalent resistor 66 may easily be connected to flow measuring equipment on the entry and exit sides. The equivalent resistor 66 is dependent on the type of inhaler used and is utilised only to adjust the flow. The equivalent resistor for the HandiHaler®, for example, is designed so as to behave in the same way as the HandiHaler® with capsule over a pressure range from about 15 to 50 cm of water column and over a flow volume from about 25 to 45 l/min.

By means of a vacuum tube 38 (Di=8 mm, length 35 cm) the connecting olive 69 at P1 of the measuring collecting tube 68 is connected to the manometer 22 integrated in the suction unit as a differential pressure measuring instrument for adjusting the pressure drop. The throughflow control valve 33 is closed and the control of the two-way magnetic valve 27 is set to "continuous". The zero point of the water column is set on the manometer 22, 29 etc and the throughflow control valve 33 is carefully opened until a water column of 40.8 cm has been achieved. The absolute pressure on both sides of the throughflow control valve (measuring points P2 and P3—see FIG. 1) is read off and documented. The regulated position of the needle valve on the throughflow control valve 33 remains unchanged. Optionally, a safety device may be provided which protects the stopcock from being accidentally moved. Once the flow rate has been applied the quotient of the pressure ratio between the pressure measuring points P3 to P2 must be less than or equal to 0.5 ("critical flow"). By replacing the adapter 67 with the appropriate equivalent resistor 66 for an adapter 64 for measuring flow, it is possible to measure and read off the throughflow rate with the flywheel flow sensor 37 (displayed for example on the measuring device integrated in the control device 89). Care must be taken to prevent the silicone connecting tube 38 (Length 50 cm, Di=12 mm) from being kinked. The air volume throughflow rate thus determined is defined as the test throughflow rate Q in liters per minute. The test throughflow rate Q has a tolerance of ±5%. The test throughflow time t in seconds is designed so that a specific volume of for example 4 liters flows through the inhaler 80. These 4 liters are specified by the EP/USP. Other volumes could easily be processed using the control unit according to the invention by suitable conversion of the suction time.

Example of the Calculation of the Suction Time:

$$\text{Suction time} = \frac{60 \text{ seconds} \times \text{suction volume required}}{\text{throughflow read off}}$$

With a flow of 39 l/min, for example, a suction time of 6.15 seconds is obtained. For different test throughflow rates different suction times for achieving a desired air volume of 4 liters are obtained.

Before actually measuring the dose delivered, the measuring collecting tube 68 is replaced by a dose collecting tube 60.

By exchanging the HandiHaler® adapter 62 for the "adapter for flow measurement" 64 and attaching it to the flywheel flow sensor 37 the flow applied can be measured as a control. The control of the two-way magnetic valve 27 is set to "timer" using the control device 89 and the calculated suction time is set using the timer setting.

The control unit is thus operated using the measuring collecting tube on the one hand and a dose collecting tube on the other hand. The measuring collecting tube serves only to adjust and determine the measuring parameters needed, whereas the dose collecting tube serves to measure the actual dose delivered. The reason for this is the quantitative multiple measurement which is required in practice. This needs a sealed and easily "cleanable" system. There is a certain potential risk of powder accumulating in the measuring collecting tube because of the P1 connector, for example, affecting both the degree of cleanliness and the accuracy of measurement. This is particularly true with measurements of trace amounts.

If the adjustment is to be carried out using an inhaler for which there is no equivalent resistor, the inhaler in question must be used and installed in the corresponding operating mode with a suitable resistance.

Figure 9:
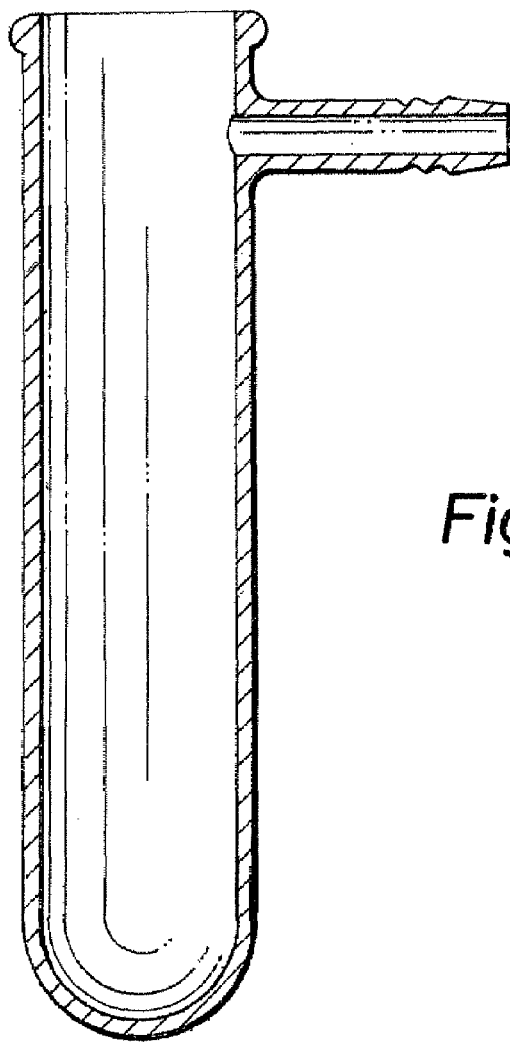
FIG. 9 shows a suction finger.
Figure 10:
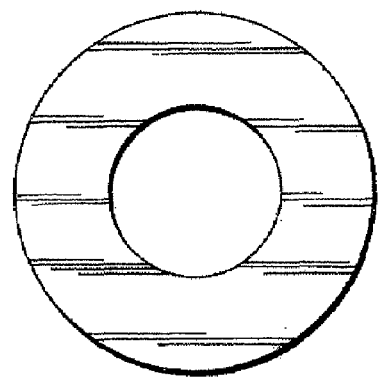
FIG. 10 shows a sealing ring.

Delivery of the Active Substance and Measurement of the Dose Delivered:

The measurement of the delivery is carried out using a dose collecting tube. Once all the operating parameters corresponding to the particular test requirements have been set in the control unit and the apparatus has been suitably checked, the inhaler 80 (e.g. the HandiHaler®) is qualified and the necessary flow has been set, the measurement of the delivery can be started. A capsule is loaded into the inhaler, the capsule is perforated and the closed inhaler is placed in the adapter 62 in the dose collecting tube 60. Then the starting button is pressed, the magnetic valve 27 is opened as a result of the time control set and the contents of the capsule are delivered by means of an emptying process. It must be ensured that the quotient of the pressures P3/P2 is less than 0.5. Deliveries from other capsules take place in the numbers specified in the test specification. The inhaler 80 is taken out after each delivery and the contents are prepared for measurement in accordance with the test procedure. Each capsule is delivered and suitably worked up in a separate dose collecting tube 60. The contents of the dose colleting tube 60 which are generally extracted are sucked into a suction finger 120 (FIG. 9) by the brief application of reduced pressure. For the suction processing the sealing ring 121 (FIG. 10) is placed between the suction finger 120 and the dose collecting tube. Quantitative measurement is usually carried out by HPLC.

Determining the Distribution of the Aerodynamic Fine Fraction:

Adjusting the flow in the cascade impactor:

The assembled cascade impactor 75 is placed upright in the dish 23 provided for it on the control unit and attached to the SIP 78. Before each measurement the impactor is tested for leaks. The SIP 78 is closed off using the closure cap 73. With the vacuum pump 84 running and the control device 89 switched on (magnetic valve permanently open) and the vacuum measuring devices 36 switched on and the throughflow control valve 33 closed, an underpressure of about 20 to 30 mbar is carefully adjusted by opening the throughflow control valve 33. The vacuum measuring device 36 at the measuring point P2 (right-hand manometer) is observed with the needle valve closed. The underpressure selected may only reduce by a maximum of 1 mbar/sec.

The flywheel flow sensor 37 is then attached to the entry to the SIP 78 by means of a connecting adapter 74 with olive for SIP and the flow volume of for example 39 liters/min which is determined and defined in the course of measuring the dose delivered is set. This ensures that both measurements, i.e. "the uniformity of the delivered dose" and the "distribution of the aerodynamic fine fraction", are carried out with the same flow. If there is no indication of the flow volume which is to be preset, it may be determined as described above with the corresponding devices in conjunction with the measuring collecting tube. In order to achieve the desired suction volume of 4 liters, for example, the suction time of 6.15 seconds calculated from the flow volume is set on the timer of the control device 89. Once the flow rate has been applied the critical throughflow (quotient P3/P2 less than or equal to 0.5) must be ensured.

In order to introduce the contents of the capsule into the impactor 75, a suitable inhaler adapter 72 with prepared inhaler 80, as described in connection with the delivery, is placed on the SIP 78. The control device has already been set to timer control. The opening of the magnetic valve 27 is effected by starting the timer on the electronic control device 89. The powder is delivered into the impactor 75. The impactor 75 is then taken apart and the residues in the inlet section (adapter 72, sample induction port 75, High Top USP 77), in the pre-separator 76, on the baffle plates of cascades 0 to 7 and on the filter are processed and measured.

The invention is not restricted to the embodiments illustrated in the drawings but within the scope of the claims also includes embodiments which make use of substitutions known in the art. These are known to the skilled man.

The invention claimed is:

1. Control unit for flow regulation for use in an apparatus for testing the delivery of a dose of powder from a powder inhaler, containing
    a first valve controllable by a time switch,
    a time switch for controlling the first valve,
    a connector connected to the first valve and allowing air to pass through,
    a throughflow control valve connected to the connector,
    a connector for a suction device provided on the first valve,
    a connector for a collecting tube or an impactor, provided on the throughflow control valve, and
    means for measuring the airflow volume through the collecting tube or an impactor,
    two connecting points for a pressure gauge provided in front of and behind the throughflow control valve in the direction of suction,
    pressure measuring gauges each mounted at the connecting point via a connecting member, wherein the connecting members include an inner capillary which carries the air and an outer tube which encases the capillary.

2. The control unit according to claim 1, wherein the means for measuring the airflow volume comprise a calibratable flow sensor.

3. The control unit according to claim 2, wherein the calibratable flow sensor is a flywheel flow sensor.

4. The control unit according to claims 2 or 3, wherein a damping filter is coupled to the collecting tube formed on the flow sensor.

5. The control unit according to one of claims 2 to 3, wherein the time switch and an apparatus for indicating the values measured by the calibratable flow sensor are integrated in a control device.

6. The control unit according to claim 4, wherein the time switch and an apparatus for indicating the values measured by the calibratable flow sensor are integrated in a control device.

* * * * *

UNITED STATES PATENT AND TRADEMARK OFFICE
CERTIFICATE OF CORRECTION

PATENT NO. : 7,604,006 B2  Page 1 of 1
APPLICATION NO. : 10/747341
DATED : October 20, 2009
INVENTOR(S) : Wolf et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1507 days.

Signed and Sealed this

Fifth Day of October, 2010

David J. Kappos
*Director of the United States Patent and Trademark Office*